United States Patent [19]

Righini et al.

[11] 4,398,790
[45] Aug. 16, 1983

[54] OPTICAL FIBER DEVICE FOR THE TRANSPORTATION AND FOCALIZATION OF LASER RADIATION

[75] Inventors: Giancarlo Righini; Vera Russo; Stefano Sottini, all of Florence, Italy

[73] Assignee: Consiglio Nazionale Delle Ricerche, Rome, Italy

[21] Appl. No.: 162,629

[22] Filed: Jun. 24, 1980

Related U.S. Application Data

[63] Continuation-in-part of Ser. No. 930,061, Aug. 1, 1978, abandoned.

[30] Foreign Application Priority Data

Aug. 1, 1977 [IT] Italy ............................... 9533 A/77

[51] Int. Cl.³ .............................................. G02B 5/14
[52] U.S. Cl. ............................. 350/96.18; 350/96.10
[58] Field of Search ............... 350/96.15, 96.18, 96.20, 350/96.10, 96.26, 96.28, 96.31; 219/121 LR

[56] References Cited

U.S. PATENT DOCUMENTS

| | | | |
|---|---|---|---|
| 3,821,510 | 6/1974 | Muncheryan | 350/96.28 |
| 4,067,937 | 1/1978 | Unno et al. | 350/96.18 |
| 4,273,109 | 6/1981 | Enderby | 350/96.26 |
| 4,305,640 | 12/1981 | Cullis et al. | 350/96.10 |

FOREIGN PATENT DOCUMENTS 1357156  6/1974  United Kingdom ............. 350/96.18

OTHER PUBLICATIONS

*Applied Optics,* vol. 14, No. 2, Feb. 1975, pp. 294–298, Paek et al., "Formation of a Spherical Lens at Optical Fiber Ends With a $CO_2$ Laser".
*IBM Technical Disclosure Bulletin,* vol. 9, No. 11, Apr. 1967, p. 1582, Steele, "Polishing of Light Fibers and Forming Ends".

*Primary Examiner*—John D. Lee
*Assistant Examiner*—Frank Gonzalez
*Attorney, Agent, or Firm*—D. Paul Weaver

[57] ABSTRACT

An optical fiber device for the transportation and focalization of laser radiation, wherein the output terminal of the device presents a convex surface which may be spherical.

9 Claims, 3 Drawing Figures

OPTICAL FIBER DEVICE FOR THE TRANSPORTATION AND FOCALIZATION OF LASER RADIATION

This is a continuation-in-part of U.S. patent application Ser. No. 930,061 filed Aug. 1, 1978 for "Optical Fiber Device For The Transportation And Focalization Of Laser Radiation", now abandoned.

BACKGROUND OF THE INVENTION

The present invention concerns an optical fiber device for the transportation and focalization of laser radiation, particularly suited for medical, surgical and biological applications.

As is well known, laser radiation may be employed for therapeutical and surgical applications. To solve the problem of energy transference from the laser output to the biological tissue to be treated, optical fibers may be utilized in the case of Nd:YAG laser, Argon laser, He-Ne laser and similar lasers. Fibers are presently available with a very low attenuation (6-10 dB/Km) suitable for transmitting powers of some tens of watts, with negligible losses and without suffering any deterioration.

In the case of known optical fibers, with plane surface termination, the laser ray departing from the fiber has its narrowest size on the output face only, becoming wider as it moves away from it. For this reason, it is necesssary to put the end face of the fiber in direct contact with the material to be treated. Otherwise, the laser power employed has to be considerably increased.

On the other hand, if the fiber is kept in contact with the target, a system for the continuous washing or cleaning of the fiber end has to be provided, whereas if the fiber is kept separated from the target, undesired effects may be produced in the area surrounding the target; moreover, the increase of the applied power causes a notable increase in the cost of the equipment.

To eliminate such drawbacks, it has been proposed to set up a suitable optical system comprising one or more lenses arranged at a convenient distance from the plane end face of the fiber, likely to focalize the laser radiation by providing an output cone of convenient width.

This system, however, encounter difficulties with the adjustment and alignment of the fiber to the optical system, in addition to size problems, rendering it ill-adapted for use in close cavities and in microsurgery.

The aim of the present invention is to provide a laser radiation, transportation and focalization system by means of an optical fiber likely to overcome the a.m. drawbacks and, therefore, particularly convenient for medical, surgical, and biological applications.

This aim is attained, according to the invention, with an optical fiber device for the transportation and focalization of laser radiation wherein the output termination of the optical fiber presents a curved convex surface which may be spherical.

Another feature of the invention is that, in the exit termination of the optical fiber, a micro-lens may be embodied, formed from material presenting a different refraction index.

Other features and advantages of the invention will become apparent during the course of the following description.

DETAILED DESCRIPTION

Figure 1:
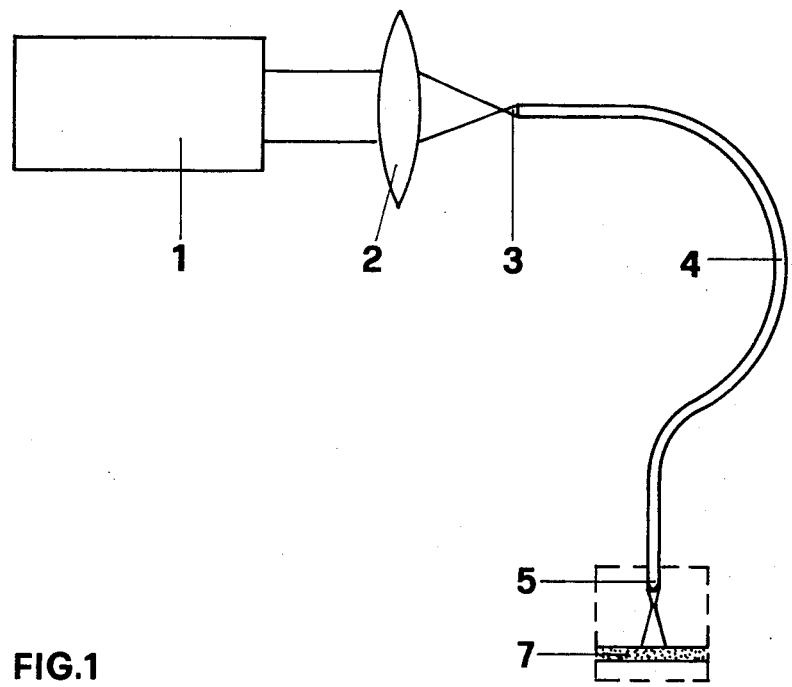
FIG. 1 is a schematic view of a device according to the invention utilizing a laser source and an optical fiber.

Referring to the drawings in detail, the device according to the invention comprises a laser radiation source 1, a conventional lens 2 (or a microscope objective) and an optical fiber 4, preferably formed from glass, quartz or plastics and of the "step-index" type, i.e. fibers in which the distribution of the core refraction index is constant. The surface of the input termination 3 and of the output termination 5 of the fiber 4 are spherical and constitute two curved dioptres.

For use of the device in medical and surgical fields, the optical fiber is inserted in a flexible sheath 6, which protects it from deterioration and breakage. The end portion of the fiber includes a long (5–10 cm) rigid hand piece, not shown, for ease of handling by the operator. The termination of the fiber is opaque to X-rays, allowing the surgeon to check, by means of X-rays, the position of the fiber's end, even when he employs it in close cavities.

Figure 2:
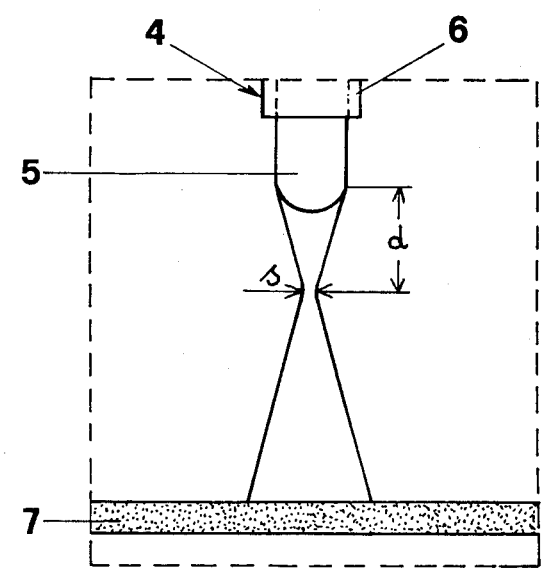
FIG. 2 is a large-scale detail of the output termination of the fiber.

The operation of the device according to the invention is as follows:

As the radiation issued from the laser source 1 is focalized by means of the lens 2, on the entry termination 3 of the fiber 4, substantially its entire energy is conveyed into the fiber. On the exit termination 5 of the fiber 4, FIG. 2, the curved dioptres focalize the departing bundle at a distance d and with a focal spot having a diameter s, which depend upon the form and the type of the dioptre and the fiber. In the focal spot, the diameter of the bundle departing from the fiber through the curved dioptre reaches its minimum size: one-third or less of the diameter of the fiber's core. As a consequence, the energy in such an area is at least ten times higher than in the case of a fiber with the usual plane termination.

By setting the terminal curved dioptre of the fiber, at a distance from the biological tissue 7, by far greater than d, the operator may just cauterize or irradiate the desired area. By approaching the fiber as far as the distance d, he may cut or destroy the biological tissue 7. The strong divergence of the bundle, created from the curved dioptre, protects the area situated below the target from any destruction.

From the foregoing, it is clearly apparent that the device according to the invention offers many advantages, particularly with respect to medical, surgical and biological applications, whereas the combination of the same advantages is not readily obtainable, at the same time, with traditional devices.

Some of the advantages of the present invention are:

It does not require any alignment between the lens and the fiber, as they form an integral.

It may operate at high power and no glue is employed in the optical system between adjacent lenses.

It has a compact structure and, due to its simple construction and low cost, may be easily replaced in its entirety.

It is easy to handle and of reduced size, and may therefore be employed in close cavities.

It may be easily applied to an endoscope.

It avoids any destruction of the tissue surrounding the target because of the strong divergence of the bundle past the focus.

It may be readily made opaque to X-rays by using one of the well known optical fiber glasses such as fuse silica or boro silicate, which are opaque to X-rays, see American Institute Of Physics Handbook, Page 6–60.

The device according to the invention is constructed from a traditional optical fiber of the "step-index" type. If the fiber is protected with a cladding, the cladding must be removed toward the end of the fiber, for a length of 1–2 mm, to carry out the shaping of the end.

When the material of the fiber is softened with heat produced by conventional means (a torch, etc.) or by a $CO_2$ laser, advantage is taken of the superficial tension, which tends to round the normally plane surface of the termination and it is then possible to shape the surface in different ways.

According to an embodiment of the invention, the focalization effect obtained by means of the curved dioptre may be improved by producing a real microlens, integral with the fiber, but presenting a different refraction index. Such a microlens is obtained by doping the end of the fiber, during the process of hot shaping, with a material presenting a refraction index different from that of the fiber. Such a special microlens operates in a similar manner to conventional lenses, presenting a different refraction index from the surrounding means. It offers, therefore, with respect to the curved dioptre having the same refraction index as the fiber, the advantage of presenting better focalization properties.

Moreover, a curved dioptre or a microlens may also be created on the entrance termination of the fiber, following the same technique. In such a case, the efficiency of the laser-fiber coupling may be increased and a laser of lower power and loser cost may be used, both of which are decided advantages.

Figure 3:
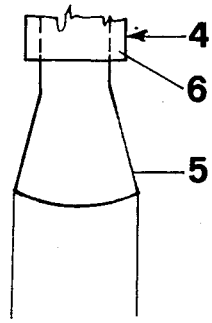
FIG. 3 is a view similar to FIG. 2 showing in detail the output termination of the fiber, in a different embodiment.

A differently-shaped lens, though based on the same inventive principle, is shown in FIG. 3. In some applications such as the biological field, the laser radiations are not expected to converge into a point, but it is sufficient that they remain parallel. In such a case, the plane surface fiber termination has to be discarded, as the bundle would unavoidably diverge. Preference is then given to a "trumpet-shaped" termination, presenting a curved convex surface. With such a termination, the rays of the departing bundle are parallel.

An exemplary embodiment of the present invention utilizes a silica glass fiber with a refraction index of 1.456. The end of the fiber is doped to create a different index of refraction at the fiber end by using powdered borax having a crystalline structure which is anisotropic with refraction along the three crystallographic axis of 1.447, 1.469, and 1.472 respectively. Practically, the refractive index obtained through powdered borax doping is an average value of the refraction indexes along the three crystallographic axis.

An alternate embodiment is achieved by utilizing as a dopant, a glass produced by the German firm of Schott. This glass is known as Schott SF6 glass and it has a refractive index of about 1.8.

A still further embodiment may be achieved by doping the fiber optic with a soda-lime glass having a refraction index of 1.512.

Regardless of which dopant is utilized, powdered borax, chips of Schott glass, or soda-lime glass, the dopant is heated to obtain a small ball having a diameter close to that of the core of fiber to be doped. Then, with a $CO_2$ laser of 3w, such as illustrated in FIG. 1, Page 295 of the Paek and A. L. Weaver article "Formation Of A Spherical Lens At Optical Fiber Ends With A $CO_2$ Laser" in Applied Optics, Volume 14, Number 2, February 1975, the small ball is put to rest and firmly kept on the head of the fiber, already shaped as a dioptre. The assembly is then heated until the fiber's head and the small ball melt to form a single block.

In an alternate production method, the fiber's end opposite the end to be doped, is fed with a 3.5w laser via a 70 to 80% coupling. The end to be doped is then brought into contact with the dopant powder or chips and the laser heat initially causes the dopant to melt. The melting continues and involves the end of the fiber which then mixes with the dopant. The duration of the application of the laser energy may be varied to vary the radius of curvature at termination from one to two times that of the fiber's radius.

Doping the end of the fiber thus has a two-fold affect. First it varies the index of refraction of the end of the fiber, and second it allows the creation of an end of the fiber having a radius of curvature remarkably different from that of the fiber core. Non-doped ends have a radius of curvature practically equal to the fiber core.

The index of refraction of the lens obtained on the fiber's end in accordance with the above procedure is a function of the quantity of the dopant used, and has a value which is an average, between the index of refraction of the fiber and that of the dopant.

In one embodiment of the invention, the index of refraction of the end of a quartz fiber, coated with plastics, is 1.456. This is the fiber type most suited to medical applications. The index of refraction of the doped end, depends on the parameters of the doping process (temperature, duration of the heating, or of the laser) and upon the type of dopant as suggested above.

Generally speaking, dopants increase the index of refraction of the fiber and bring it to an intermediate value between that of the non-doped fiber and that of the pure dopant. Thus, if the index of refraction of the fiber is 1.456 as suggested above, and Schott SF6 glass is used as a dopant having a refraction index of 1.8, the doped lens formed in the end of the glass fiber will have an increase in the index of refraction above that of the fiber which may be as great as 0.2 or approximately 1.628, depending upon the parameters of the doping process used.

The doping of the fiber ends has a two-fold affect. It increases the index of refraction of the fiber by transforming the dioptre into a lens and it allows the fiber end to be shaped so that it has a diameter greater than that of the fiber core. As a result, it is possible to obtain variations in the focal length up to more than one size order and according to diagrammatic representations of radiations which have been delineated, the doping of the fiber causes the widening of the radiation cone to more than one size order.

A trumpet-shaped end may be achieved by using a quartz rod having a diameter equal to the desired maximum diameter of the trumpet. The rod is melted in accordance with known techniques and submitted to traction to obtain a fiber. The portion where the original rod is transformed into the final fiber is the trumpet. Variations in the traction speed may be used to vary the angle of the trumpet walls and the point of severance varies the diameter within the boundaries of the diameter of the original quartz rod and the ultimate diameter of the fiber. This process is known and has been performed by G. Nath of the Max Planck Institute of Munic in the German Federal Republic since at least 1977.

If the invention is to be used for medical purposes, the fiber optic cladding is generally plastic. It is removed at the end of the fiber by traditional chemical milling or mechanical methods.

If the cladding is other than plastic, traditional chemical or mechanical milling techniques may also be used.

It is to be understood that the form of the invention herewith shown and described is to be taken as a preferred example of the same, and that various changes in the shape, size and arrangement of parts may be resorted to, without departing from the spirit of the invention or scope of the subjoined claims.

We claim:

1. An optical fiber device for the transportation and focalization of laser radiation, comprising a single optical fiber having a core made of glass or quartz and including entrance and exit terminals, wherein said exit terminal is a convex surface formed in the optical fiber material and doped to create an index of refraction axially different than the main body of the optical fiber; and said exit terminal of the optical fiber device is a microlens incorporated into the fiber, the radius of curvature of which is controlled by the amount of dopant used to create said axially different index of refraction.

2. An optical fiber device as defined in claim 1, wherein said convex surface is spherically curved.

3. An optical fiber device as defined in claim 1, wherein both said entrance and exit terminals of the optical fiber device are convex.

4. An optical fiber device as defined in claim 1, wherein both said entrance and exit terminals of the optical fiber device are spherically curved.

5. An optical fiber device as defined in claim 1, wherein said entrance and exit terminals of the optical fiber device are trumpet-shaped.

6. An optical fiber device as defined in claim 1, wherein the optical fiber of said device is protected by a flexible sheath.

7. An optical fiber device as defined in claim 6, wherein said exit terminal portion of the optical fiber is provided with a rigid sleeve.

8. An optical fiber device as defined in claim 7, wherein said exit terminal portion of the optical fiber device is opaque to X-rays.

9. An optical fiber device as defined in claim 1 wherein said dopant created index of refraction is up to and including 0.2 greater than the index of refraction of the main body of the optical fiber.

* * * * *